(12) United States Patent
Goering

(10) Patent No.: US 11,844,297 B2
(45) Date of Patent: Dec. 19, 2023

(54) IN-FIELD SOIL ANALYSIS SYSTEM AND METHOD

(71) Applicant: Deere & Company, Moline, IL (US)

(72) Inventor: Kevin J. Goering, Cambridge, IA (US)

(73) Assignee: DEERE & COMPANY, Moline, IL (US)

( * ) Notice: Subject to any disclaimer, the term of this patent is extended or adjusted under 35 U.S.C. 154(b) by 347 days.

(21) Appl. No.: 16/897,997

(22) Filed: Jun. 10, 2020

(65) Prior Publication Data

US 2021/0386011 A1    Dec. 16, 2021

(51) Int. Cl.
*G01N 21/84*    (2006.01)
*A01C 21/00*    (2006.01)
(Continued)

(52) U.S. Cl.
CPC .......... *A01C 21/007* (2013.01); *A01C 21/005* (2013.01); *G01N 21/359* (2013.01);
(Continued)

(58) Field of Classification Search
CPC ................ A01C 21/007; A01C 21/005; G01N 21/3563; G01N 21/359; G01N 21/84;
(Continued)

(56) References Cited

U.S. PATENT DOCUMENTS

| 8,655,601 B1* | 2/2014 | Sridhar ................. G01N 21/25 702/30 |
| 10,165,725 B2* | 1/2019 | Sugumaran .......... A01B 79/005 |

(Continued)

FOREIGN PATENT DOCUMENTS

| IN | 201741040710 A | 11/2018 |
| WO | WO2019111527 A1 | 6/2019 |

(Continued)

OTHER PUBLICATIONS

Extended European Search Report and Written Opinion issued in European Patent Application No. 21173629.3, dated Nov. 9, 2021, in 08 pages.

(Continued)

*Primary Examiner* — Isiaka O Akanbi
(74) *Attorney, Agent, or Firm* — KLINTWORTH & ROZENBLAT IP LLP

(57) ABSTRACT

A soil analysis system is provided for an agricultural vehicle and includes a sensor apparatus, a controller, and a display device. The sensor apparatus includes a location sensor configured to determine a location of the agricultural vehicle; and an infrared sensor configured to collect infrared spectra from soil at the location. The controller is configured to determine a soil type based on the location; select at least one nutrient calibration curve based on the soil type at the location; analyze the infrared spectra according to the at least one nutrient calibration curve to generate at least one estimated nutrient value for the soil at the location; and generate display commands representing the at least one estimated nutrient value. The display device is configured to generate a first display representing the at least one estimated nutrient value based on the display commands.

20 Claims, 8 Drawing Sheets

(51) Int. Cl.
*G01N 21/3563* (2014.01)
*G01N 21/359* (2014.01)
*G01N 33/24* (2006.01)
*G01S 19/01* (2010.01)

(52) U.S. Cl.
CPC ......... *G01N 21/3563* (2013.01); *G01N 21/84* (2013.01); *G01N 33/24* (2013.01); *G01S 19/01* (2013.01); *G01N 2033/245* (2013.01)

(58) Field of Classification Search
CPC ............. G01N 33/24; G01N 2033/245; G01N 21/3554; G01N 21/55; G01S 19/01; A01B 47/00; A01B 79/02; A01B 79/005
USPC ..................................... 356/300, 237.2–237.6
See application file for complete search history.

(56) References Cited

U.S. PATENT DOCUMENTS

| | | | | |
|---|---|---|---|---|
| 10,362,733 | B2* | 7/2019 | Birrell | A01D 41/127 |
| 10,485,161 | B2* | 11/2019 | Connell | A01B 49/06 |
| 2003/0019152 | A1* | 1/2003 | Raun | A01C 21/007 47/58.1 SC |
| 2011/0102798 | A1* | 5/2011 | Holland | A01B 79/005 356/445 |
| 2015/0373905 | A1* | 12/2015 | Anderson | A01C 21/00 701/33.9 |
| 2016/0180473 | A1 | 6/2016 | Groeneveld | |
| 2018/0035605 | A1 | 2/2018 | Guan et al. | |
| 2018/0092295 | A1* | 4/2018 | Sugumaran | A01C 21/00 |
| 2018/0098495 | A1* | 4/2018 | Van Meurs | A01C 7/105 |
| 2018/0120133 | A1 | 5/2018 | Blank et al. | |
| 2018/0124992 | A1 | 5/2018 | Koch et al. | |
| 2018/0190045 | A1* | 7/2018 | Richard | B62D 55/14 |
| 2018/0310464 | A1 | 11/2018 | Zemenchik et al. | |
| 2019/0124825 | A1* | 5/2019 | Anderson | A01C 23/024 |
| 2019/0150357 | A1* | 5/2019 | Wu | G06T 7/73 |
| 2019/0261551 | A1 | 8/2019 | Yoshida et al. | |
| 2021/0173399 | A1* | 6/2021 | Richard | B60W 40/12 |

FOREIGN PATENT DOCUMENTS

| | | | |
|---|---|---|---|
| WO | WO-2019166992 A2 * | 9/2019 | ........ A01C 21/002 |
| WO | WO2019166992 A2 | 9/2019 | |

OTHER PUBLICATIONS

Mathias Steiner, IBM Research-Brazil, No Farms, No Food, AI-Powered Technology Will Help Farmers Check Soil and Water, Sep. 5, 2018.

Deere & Company, John Deere Precision Ag Technology Brochure, Oct. 2015.

Deere & Company, John Deere HarvestLab 3000, HarvestLab and Constituent Sensing, undated admitted prior art.

IBM, AgroPad—AI Powered Technology Will Help Farmers Health-Check Soil and Water, YouTube, Sep. 5, 2018.

* cited by examiner

IN-FIELD SOIL ANALYSIS SYSTEM AND METHOD

CROSS-REFERENCE TO RELATED APPLICATION(S)

Not applicable.

STATEMENT OF FEDERALLY SPONSORED RESEARCH OR DEVELOPMENT

Not applicable.

FIELD OF THE DISCLOSURE

This disclosure relates to a soil analysis system and method for an agricultural operation, particularly to an in-field work vehicle system and method used for analyzing the soil.

BACKGROUND OF THE DISCLOSURE

Effective and efficient agricultural operation is highly dependent on reliable knowledge of soil nutrients and other soil characteristics. Such nutrients and other characteristics may vary not only from region to region, but also between smaller areas within a single field. It is beneficial for an operator to understand the various soil characteristics across the field.

SUMMARY OF THE DISCLOSURE

The disclosure provides an in-field soil analysis system and method.

In one aspect, a soil analysis system is provided for an agricultural vehicle and includes a sensor apparatus, a controller coupled to the location sensor and the infrared sensor, and a display device coupled to the controller. The sensor apparatus includes a location sensor configured to determine a location of the agricultural vehicle; and an infrared sensor configured to collect infrared spectra from soil at the location. The controller is configured to determine a soil type based on the location; select at least one nutrient calibration curve based on the soil type at the location; analyze the infrared spectra according to the at least one nutrient calibration curve to generate at least one estimated nutrient value for the soil at the location; and generate display commands representing the at least one estimated nutrient value. The display device is configured to generate a first display representing the at least one estimated nutrient value based on the display commands.

In another aspect, a soil analysis system is arranged on-board an agricultural vehicle. The soil analysis system includes a controller having a processor and memory coupled to the processor and storing instructions. The processor executes the stored instructions to receive a first sensor-based data set with first infrared spectra collected by a sensor apparatus at a first location within a field; determine a first soil type associated with the first location; select a first calibration curve corresponding to the first soil type at the first location; apply the first calibration curve to the first infrared spectra to generate a first estimated nutrient value for the first location; generate a fertilizer recommendation based on the first estimated nutrient value for the first location; and generate actuator signals to selectively apply a fertilizer onto the field at the first location based on the fertilizer recommendation.

In a further aspect, a method is provided for analyzing soil on-board an agricultural vehicle within a field. The method includes the steps of: collecting, with an infrared sensor, infrared spectra from the soil at a first location; identifying, with a location sensor, the first location; determining a soil type for the soil based on the first location; selecting at least one nutrient calibration curve based on the soil type at the first location; applying the at least one nutrient calibration curve to the infrared spectra in order to generate at least one estimated nutrient value for the soil at the first location; and displaying, on a display device, the at least one estimated nutrient value The details of one or more embodiments are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION

Figure 1:
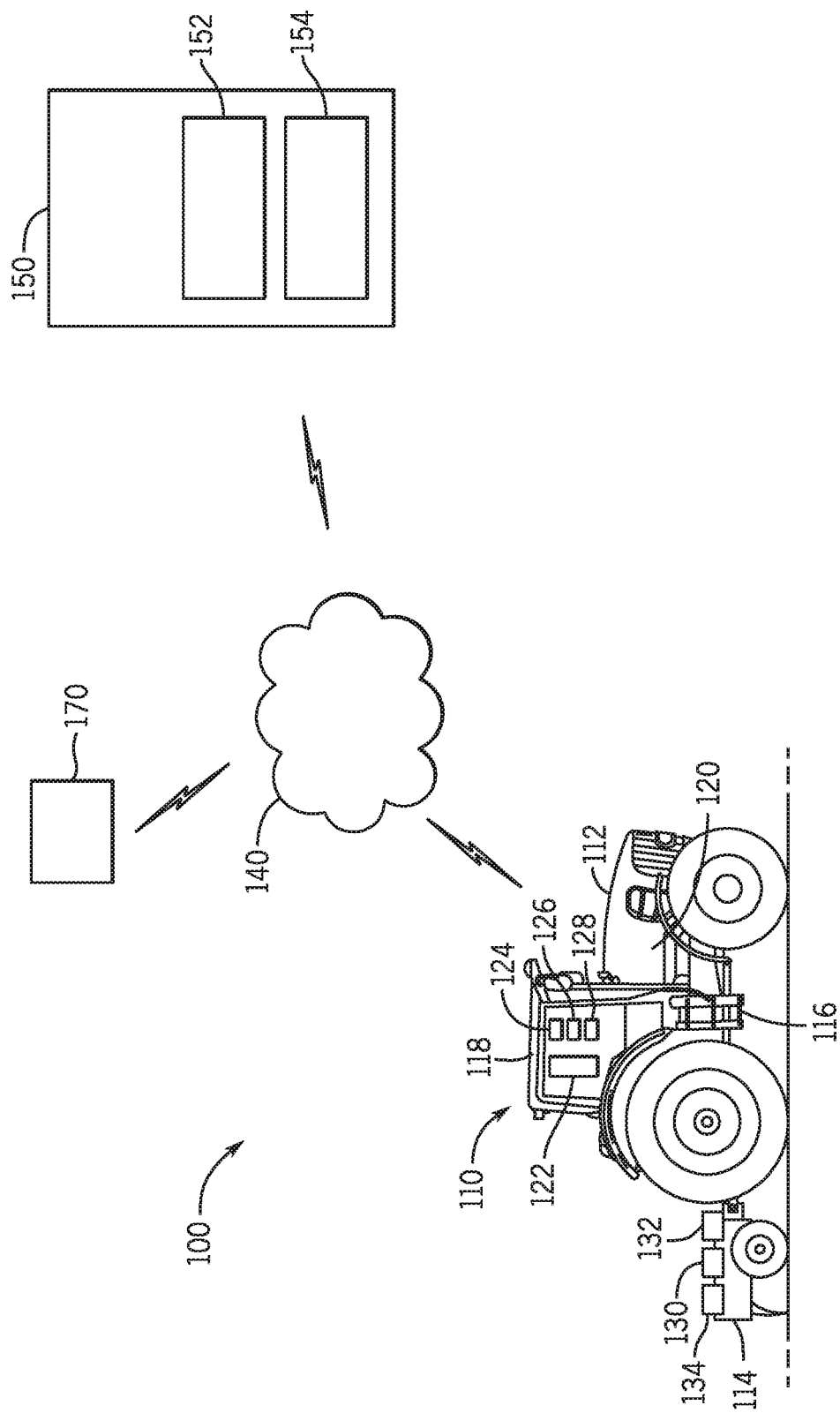
FIG. 1 is a schematic view of an environment for implementing a soil analysis system with an agricultural work vehicle according to an example embodiment.

The following describes one or more example embodiments of the disclosed system and method, as shown in the accompanying figures of the drawings described briefly above. Various modifications to the example embodiments may be contemplated by one of skill in the art.

An operator may use a work vehicle in the form of an agricultural planting vehicle to plant seeds, seedlings, plants, root stock, bulbs, or other crop precursors in rows over a field during a planting event. Clearly, it is beneficial for an operator to know and understand the soil characteristics of the field, including soil type and constituent nutrients. Such characteristics may vary based on geographic region, and moreover, may vary greatly within the field. Determining such soil information may be challenging. Laboratory testing may be expensive, particularly without a clear understanding of the specific field areas at which to test. Some commercial characteristic mapping services may be generally available, but typically, only with respect to broad geographical regions.

The present disclosure generally relates to a system and method for analyzing soil within a field of an operator, more specifically for identifying, evaluating, and classifying of soil characteristics, particularly soil nutrients, and recommending responses to such soil characteristics. Generally, the system and method may be primarily implemented within a field, representing a relatively small area (e.g., as opposed to a state or national region) in an agricultural operation. However, portions may be implemented with a soil analysis center and/or based on knowledge from external sources and/or with information from other operators. The system and method may be at least partially implemented during an agricultural operation with soil engagement, e.g. planting, tilling, or closing operations, in which soil is analyzed in approximately real time or in which soil data is collected, stored, and subsequently analyzed.

As described in greater detail below, the soil analysis system and method may collect and consider sensor information associated with soil at a location. The information collected by the sensor apparatus may include near-infrared spectra reflected by the soil and/or mid-infrared spectra reflected by the soil, as well as other soil parameters such as temperature, pH, moisture, and the like. Collectively, the soil information at the particular location may be considered a sensor-based soil data set. The sensor-based soil data sets may be evaluated with respect to soil type (and other parameters) by identifying one or more wavelength peaks associated with particular nutrients or other soil characteristics and application of one or more calibration curves to quantify or qualify the nature of the nutrients or other soil characteristics. In turn, and upon consideration of multiple sensor-based data sets, the soil analysis system and method may generate nutrient zone maps with nutrient zones and may further generate recommendations in response to the nutrient zone maps. Further, the soil analysis system and method may recommend soil locations for collection of soil samples for laboratory analysis to generate laboratory-based soil data sets with information such as collection location, near-infrared spectra reflected by the soil, mid-infrared spectra reflected by the soil, additional soil parameters, and in particular, nutrient and other characteristic values as determined by the laboratory (e.g., with chemical and/or a more thorough mass spectrometry analysis). The soil analysis system and method may use the laboratory-based soil data sets and resulting nutrient and characteristic values to modify the calibration curves used for analyzing the sensor-based data sets.

In some examples, the soil analysis system and method may use soil type as a criterium for selection of the calibration curve for analyzing a sensor-based soil data set. Generally, soil type is defined by the dominating size of the particles within the soil, such as sand, clay, silt, peat, chalk and loam types of soil. Soil type may have various types of classification nomenclature. For example, the US Department of Agriculture (USDA) defines soil taxonomy with six hierarchical levels (suborder, great group, subgroup, family, and series) that define soils based on relative sand, silt, and clay percentages, as well as other characteristics. Generally, the soil type from the USDA is based on historical sampling.

The following describes one or more example implementations of the disclosed soil analysis systems and methods for a field, as shown in the accompanying figures of the drawings described briefly above. Generally, the disclosed systems and methods operate in the context of an agricultural work machine in order to monitor, evaluate, and display soil information that provide for improved efficiency, operation, and production as compared to conventional systems and techniques.

FIG. 1 is an example environment in which an in-field soil analysis system 100 may be implemented in order to monitor, display, evaluate, and/or advise on crop soil nutrients and other characteristics. Generally, the in-field soil analysis system 100 may be implemented in, or associated with, one or more work vehicles 110 (one of which is shown) and/or data and/or processing sources 150, 170, including a soil analysis center 150, and a soil type mapping database 170, that may communicate over a network 140. Although one work vehicle 110 is depicted in FIG. 1 and discussed in greater detail below as an example, the in-field soil analysis system 100 may be used with respect to any number of vehicles performing the same or different work functions as further data sources to improve the soil analysis discussed below. In various examples, the in-field soil analysis system 100 may be part of a distributed system (e.g., with the soil analysis center 150, the soil type mapping database 170, personal computing devices, and/or other vehicles cooperating with vehicle 110) and/or a stand-alone system. In some examples, the soil analysis center 150 and soil type mapping database 170 may be omitted. An introduction of the work vehicle 110, the soil analysis center 150, and the soil type mapping database 170, will be provided below prior to a more detailed description of operation of the in-field soil analysis system 100.

In one embodiment, the work vehicle 110 is in the form of a tractor 112 that tows a planting apparatus 114 (e.g., such that the work vehicle 110 may be considered an agricultural planting vehicle or planter). The tractor 112 has a vehicle frame 116 supporting the cab 118, and generally, the tractor 112 includes a powertrain 120 supported on the frame 116 that generates power for propulsion and/or other tasks to be performed by the work vehicle 110. In one example, the powertrain 120 may include an engine, transmission, steering system, wheels, and the like for propelling and maneuvering the work vehicle 110, either autonomously or based on commands by the operator. The work vehicle 110 may include various other components or systems that are typical on work vehicles. Examples include actuation systems, lubrication and cooling systems, battery systems, exhaust treatment systems, braking systems, and the like.

In this example, the planting apparatus 114 is towed behind the tractor 112 to dispense seeds, root stocks, or crop precursors as the work vehicle 110 traverses the field, either automatically or based on commands from the operator. As such, the planting apparatus 114 may include any suitable components, including supply bins, actuators, controllers, frames, valves, wheels, openers, tanks, meters, shanks, and the like. It should be noted that the soil analysis system 100 may be used with respect to any suitable vehicle, planting apparatus, agricultural machine or vehicle, or other type of work vehicle or machine. In particular, and as discussed in greater detail below, the planting apparatus 114 may include one or more openers or shanks that engage with the soil as the vehicle 110 traverses the field, thereby enabling the soil analysis system 100 to interact with the soil for collection of soil data, as described below.

The work vehicle 110 may further include a vehicle controller 122 (or multiple controllers) to control various aspects of the operation of the work vehicle 110. For example, the vehicle controller 122 may also facilitate automatic or manual maneuvering of the vehicle traversing the field and actuation of the planting apparatus 114 during a planting event. Additionally, in some embodiments, the vehicle controller 122 may implement any or all (or none) of the functions of the soil analysis system 100 discussed herein.

Generally, the vehicle controller 122 (or others) may be configured as a computing device with associated processor devices and memory architectures, as a hard-wired computing circuit (or circuits), as a programmable circuit, as a hydraulic, electrical or electro-hydraulic controller, or otherwise. As such, the vehicle controller 122 may be configured to execute various computational and control functionality with respect to the work vehicle 110, the tractor 112, the planting apparatus 114, and/or the soil analysis system 100. In some embodiments, the vehicle controller 122 may be configured to receive input signals in various formats from a number of sources (e.g., including from the operator via operator input devices 124, one or more sensor apparatuses 130, units, and systems onboard or remote from the work vehicle 110, and/or other aspects of the soil analysis system 100); and in response, the vehicle controller 122 generates one or more types of commands for implementation by the various systems on or outside the work vehicle 110.

As one example discussed in greater detail below, the vehicle controller 122 may facilitate operation of the soil analysis system 100, particularly with respect to collecting, evaluating, displaying, sending, and making recommendations associated with soil information. Initially, the collected soil data may be in the form of raw data from the sensor apparatus 130 described below (or other sources) or undergo some processing in the vehicle controller 122 in order to extract the desired characteristics or parameters. Moreover, in some examples, the vehicle controller 122 may also implement one or more aspects of the soil analysis system 100 described below with respect to the soil analysis center 150 and/or the soil type mapping database 170. Further details will be provided below.

In some embodiments, the vehicle controller 122 may be configured to receive input commands and to interface with an operator via human-vehicle interfaces in the forms of one or more operator input devices 124 and/or one or more display devices 126, which may be disposed inside the cab 118 of the work vehicle 110 for easy access by the vehicle operator. The operator input devices 124 may be configured in a variety of ways. In some embodiments, the one or more operator input devices 124 may include devices with one or more joysticks, various switches or levers, one or more buttons, a touchscreen interface, a keyboard, a speaker, a microphone associated with a speech recognition system, or various other human-machine interface devices. As described in greater detail below, the operator may use the operator input devices 124 to steer the work vehicle 110 during an agricultural event, to interact with the planting apparatus 114, and/or to interact with the soil analysis system 100 and the display device 126 to view soil analysis information. The display device 126 may be implemented as a flat panel display or other display type that is integrated with an instrument panel or console of the work vehicle 110. The display device 126 may include any suitable technology for displaying information, including, but not limited to, a liquid crystal display (LCD), light emitting diode (LED), organic light emitting diode (OLED), plasma, or a cathode ray tube (CRT). As described in greater detail below, the display device 126 may function to render one or more types of soil information generated in accordance with operation of the soil analysis system 100.

The work vehicle 110 further includes a vehicle communication component 128. The vehicle communication component 128 enables communication between the vehicle controller 122, the soil analysis center 150, soil type mapping database 170, and other information sources. The vehicle communication component 128 includes any suitable system for sending and/or receiving data, including directly (e.g., via Bluetooth®, radio frequency signals, or the like) or via network 140. Thus, the vehicle communication component 128 may include a network interface or adapter, a Bluetooth® transceiver, a radio transceiver, a cellular transceiver, an LTE transceiver and/or a Wi-Fi transceiver. The network 140 may include or otherwise cooperate with the JDLink™ system commercially available from Deere & Company of Moline, Illinois.

The work vehicle 110 further includes one or more sensor apparatuses 130 on the tractor 112 and/or planting apparatus 114 that function to collect information associated with the work vehicle 110 and the associated environment. Such information may be provided to the vehicle controller 122 and/or the vehicle communication component 128 for potential transmission and use by the soil analysis system 100. In one example, discussed below, the sensor apparatus 130 includes a location or position sensor, a light source, a near-infrared sensor, a mid-infrared sensor, and one or more auxiliary sensors that collectively function to facilitate generation of sensor-based soil data sets, discussed below. Other sensors and associated components may be provided.

Additionally, the work vehicle 110 may include a sampling mechanism 132 for selectively collecting a portion of soil material as the vehicle 110 traverses the field. The sampling mechanism 132 may include a scoop or a coring device that is actuated to engage the soil, collect the sample, and store the sample. As described below, the collected sample may be laboratory tested (e.g., chemically tested in some manner on the vehicle, by the operator, or by a third party). In one example, the sampling mechanism 132 may be onboard the work vehicle 110 with the other aspects of the soil analysis system 100 discussed herein, while in other examples, the sampling mechanism 132 may be located on another vehicle or machine, or the sampling mechanism 132 may be omitted and collection may be manually performed by the operator or other party.

In some examples, the work vehicle 110 may further include a fertilizer applicator 134 that operates to distribute fertilizer (generally, any type of nutrient) onto or into the field. The fertilizer applicator 134 may operate based on actuator commands or signals from the controller 122 generated automatically in response to soil analysis and/or based on commands from the operator via the input devices 124. Any suitable type of fertilizer applicator 134 may be provided for distributing any type or form of fertilizer, including spinner spreaders, air booms, side-dress rigs, top-dress applicators, and the like for distributing solid, liquid, or gaseous forms of fertilizer. As discussed in greater detail below, the soil analysis system 100 may operate to selectively direct an appropriate amount of fertilizer to each individual location at which sensor data is collected.

It should be noted that various aspects of the work vehicle 110 that interact with the soil analysis system 100 and other vehicle systems may be embodied as a personal device associated with the vehicle operator and/or the work vehicle 110. Such aspects may include one or more functional units of the vehicle controller 122, operator input device 124, display device 126, vehicle communication component 128, and sensor apparatus 130. Such devices implementing the soil analysis system 100 associated with the work vehicle 110 may include servers, desktop computers, laptop computers, tablet computers, or other mobile devices, such as palm top computers, cell phones, smart phones, multimedia players, personal digital assistants, etc.

As noted above, the soil analysis center 150 may be in communication with the work vehicle 110 to implement one or more functions of the soil analysis system 100, such as to receive and evaluate soil information from one or more operators to facilitate one or more aspects of the soil analysis system 100, discussed below. In some examples, the soil analysis center 150 may operate as "backend" system or server that facilities operation within a field or fields, including the collection and creation of various types of data.

Generally, the soil analysis center 150 may be considered to have at least one soil analysis center controller 152 and at least one communication component 154, as well as data stores, interface components, and the like (not shown in FIG. 1). In one example, the soil analysis center controller 152 and soil analysis center communication components 154 may have similar elements, characteristics, and functionality to the vehicle controller 122 and vehicle communication component 128, respectively, as discussed above. As such, the soil analysis center controller 152 is in communication with the work vehicle 110 via the soil analysis center communication component 154 over a suitable interconnection architecture or arrangement that facilitates transfer of data, commands, power, etc., such as network 140, to implement one or more aspects of the soil analysis system 100, including providing requested or desired data for carrying out the associated functions. In some examples, the soil analysis center 150 may be omitted.

Briefly, in one example, the system 100 may include or otherwise interact with a soil type mapping database 170 as a data source in which soil types are stored according to location. In one example, the soil type mapping database 170 maintained by the USDA. Other types of external databases and systems may also be accessed by the soil analysis system 100.

Figure 2:
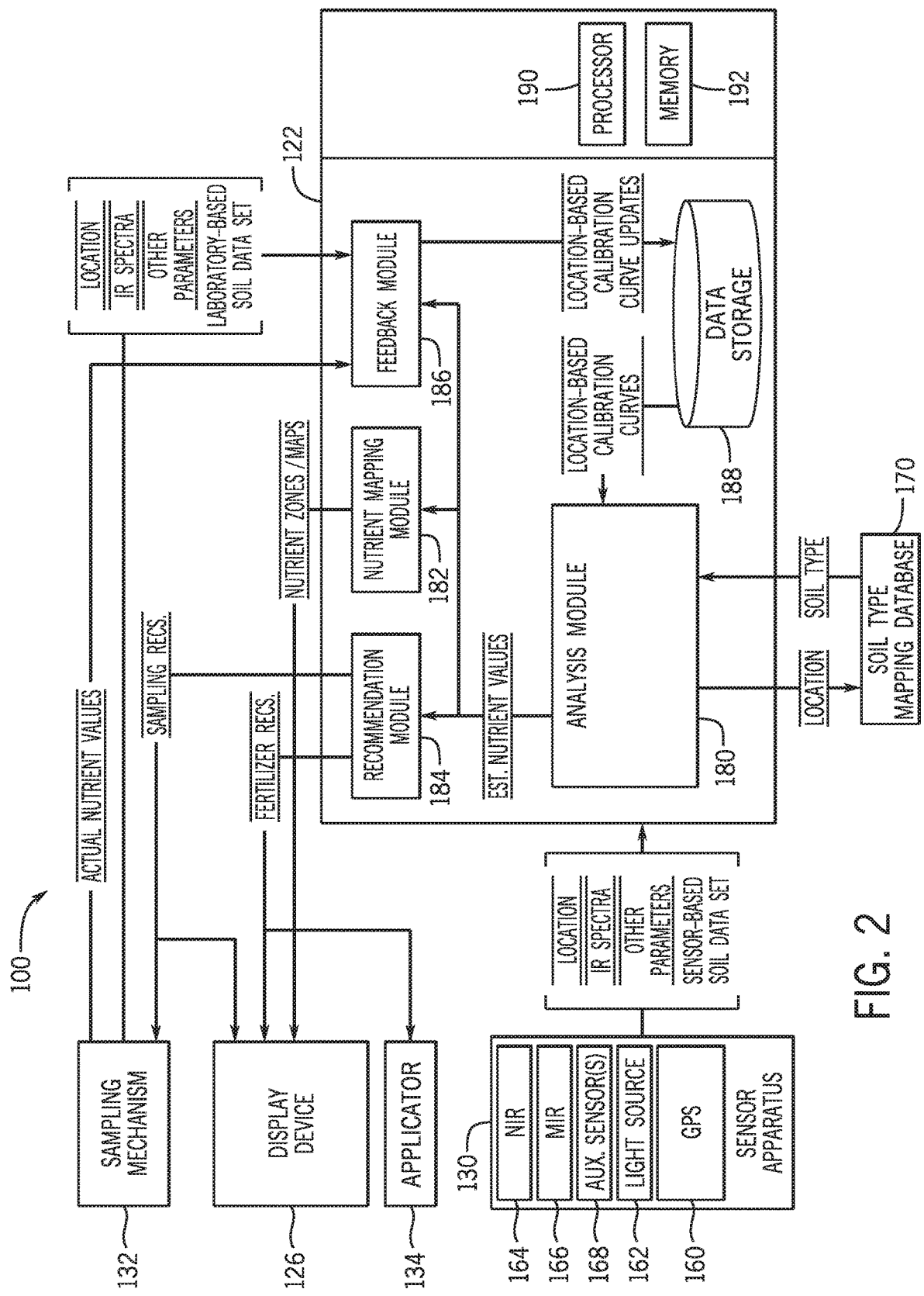
FIG. 2 is a schematic block diagram of the soil analysis system of FIG. 1 according to an example embodiment.

The view of FIG. 2 provides an example schematic operation of the soil analysis system 100 with dataflows into, out of, and within the vehicle controller 122, as well as the display device 126, the sensor apparatus 130, the sampling mechanism 132, and applicator 134. As also shown in FIG. 2, the soil analysis system 100 may include or interact with a soil type mapping database 170, as introduced above and as discussed in further detail below.

Generally, the soil analysis system 100 may be considered to include the controller 122, the sensor apparatus 130, and display device 126. The soil analysis system 100 may optionally include a sampling mechanism 132, applicator 134, and one or more additional controllers, such as center controller 152, and data sources, such as a soil type mapping database 170.

The view of FIG. 2 additionally provides further details about one example of the sensor apparatus 130. As shown, the sensor apparatus 130 includes a positioning system device (or other type of location device) 160, a light source 162, a near-infrared sensor 164, a mid-infrared sensor 166, and one or more auxiliary sensors 168. As introduced above, one or more portions of the sensor apparatus 130 may be positioned proximate to the soil such that data associated with the soil may be collected. One or more collected parameters at a location may form a sensor-based data set.

In one example, the location device 160 may be any type of satellite positioning system device (e.g., Global Positioning System (GPS) in the United States or other satellite positioning systems used in other parts of the world). Generally, the location device 160 operates to ascertain a location for the work vehicle 110 within the field, particularly when collecting information making up the soil data sets.

The light source 162 may be any suitable type of light source that functions to illuminate the area proximate to the engaged soil to enable operation of the near-infrared sensor 164 and mid-infrared sensor 166. The near-infrared sensor 164 operates to detect the reflectance of light from the soil within the near-infrared spectrum; and the mid-infrared sensor 166 operates to detect the reflectance of light from the soil within the mid-infrared spectrum. In one example, the near-infrared spectrum may be considered wavelengths between 700 nm and 2500 nm, and the mid-infrared spectrum may be considered wavelengths between 2500 nm and 25000 nm, although the ranges for analysis may vary. Various prisms and fiber optic components may be provided as part of the sensor apparatus 130 to facilitate collection of the data.

The auxiliary sensors 168 may include additional soil or environmental sensors, including one or more moisture sensors, one or more pH sensors, and/or one or more temperature sensors. As discussed below, the sensor apparatus 130 functions to collect information associated with the soil, and particularly generates infrared spectra and other parameters (e.g., moisture, pH, temperature, etc.) at a collection location as a sensor-based soil data set. Additional details are provided below.

In this example, the vehicle controller 122 may be considered to be organized as one or more functional units or modules 180, 182, 184, and 186 (e.g., software, hardware, or combinations thereof), as well as one or more types of data storage 188. As an example, each of the modules 180, 182, 184, 186 and data storage 188 may be implemented with processing architecture such as a processor 190 and memory 192. For example, the controller 122 may implement the modules 180, 182, 184, 186 and data storage 188 with the processor 190 based on programs or instructions stored in memory 192. In the depicted embodiment, the modules 180, 182, 184, 186 include an analysis module 180, a nutrient mapping module 182, a recommendation module 184, and a feedback module 186. Generally, the data storage 188 may function to store location-based calibration curves, as well as to store and/or enable accessibility of one or more of the other types of data discussed below.

The data flows and organization depicted in FIG. 2 are merely examples, and other mechanisms for performing similar functions may be provided, certain functions may be omitted, and additional functions may be added. Moreover, although depicted in the vehicle controller 122, one or more of the modules 180, 182, 184, 186, the data storage 188, and other operational functionality described below may be implemented within the vehicle controller 122 or within a separate device (e.g., such as a personal computer, smartphone, or the like). In some examples, the soil analysis center controller 152 may also receive similar data and perform similar operations with respect to the other work vehicles associated with the field of the operator or in other fields. Additional details about operation of these modules 180, 182, 184, 186 and data storage 188 will be provided below with reference to FIGS. 1 and 2.

From the context of the work vehicle 110, implementation of the soil analysis system 100 may be enabled or activated in a number of ways. In one example, the first work vehicle 110 may collect soil data and other types of data based on a manual activation by the operator (e.g., via the operator input device 124). In further examples, the work vehicle 110 may implement the soil analysis system 100 based on an automatic activation, e.g., upon crossing a geographical boundary, upon actuation the planting apparatus 114, or upon actuation of another type of soil engaging activity.

Figure 3:
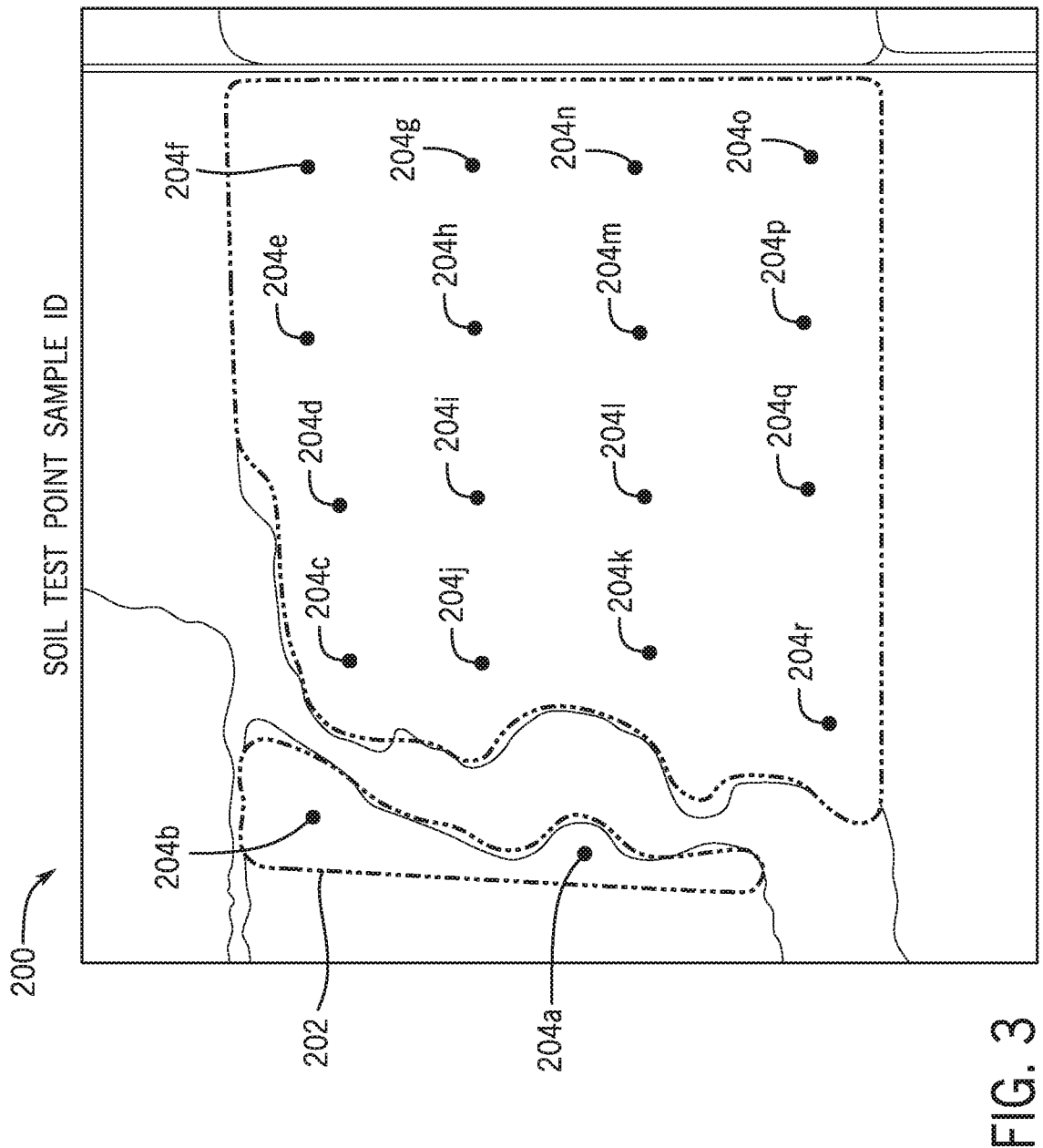
FIG. 3 is an example field in which the soil analysis system of FIG. 2 may be implemented according to an example embodiment.

Reference is briefly made to FIG. 3, which is schematic view of an example field 200 in which the soil analysis system 100 is implemented. In this example, the field 200 is depicted with defined outer boundaries 202 within which a number of sensor-based soil data sets have been collected of the soil while remaining situated in the ground of the field 200 at locations 204a-204r for consideration by the system 100, described below. The locations 204a-204r associated with the sensor-based soil data sets may be selected for any suitable reason, including time or distance frequencies, geographical spacings, and/or based on recommendations.

As introduced above, during operation, the sensor apparatus 130 generates sensor-based soil data sets, each set with the location, infrared spectra, and other parameters, that are received by the controller 122. In other words, the locations 204a-204r depicted in FIG. 3 represent sensor-based soil data sets collected over time. In the discussion below, the analysis of the sensor-based data sets may be performed in real time or collectively.

Although not shown, the controller 122 may include an input module or unit configured to condition and/or distribute the sensor-based data sets and other data received by controller 122. For example, the data may be filtered, identified, sorted, and the like prior to being distributed to the modules 180, 182, 184, 186 and/or data storage 188.

In one example, the analysis module 180 receives and considers the sensor-based soil data set. Based on the location associated with soil data set, the analysis module 180 may determine a soil type associated with the location at which the soil data set was collected. In one example and as shown in FIG. 2, the analysis module 180 may send the location to the soil type mapping database 170, and in return, receive a soil type for the location or a soil type map for the field from which the soil type for the location may be determined. In a further example, the soil type map for the field may be retrieved from data storage 188 such that the analysis module 180 may determine the soil type for the location without using an external database such as the soil type mapping database 170.

Figure 4:
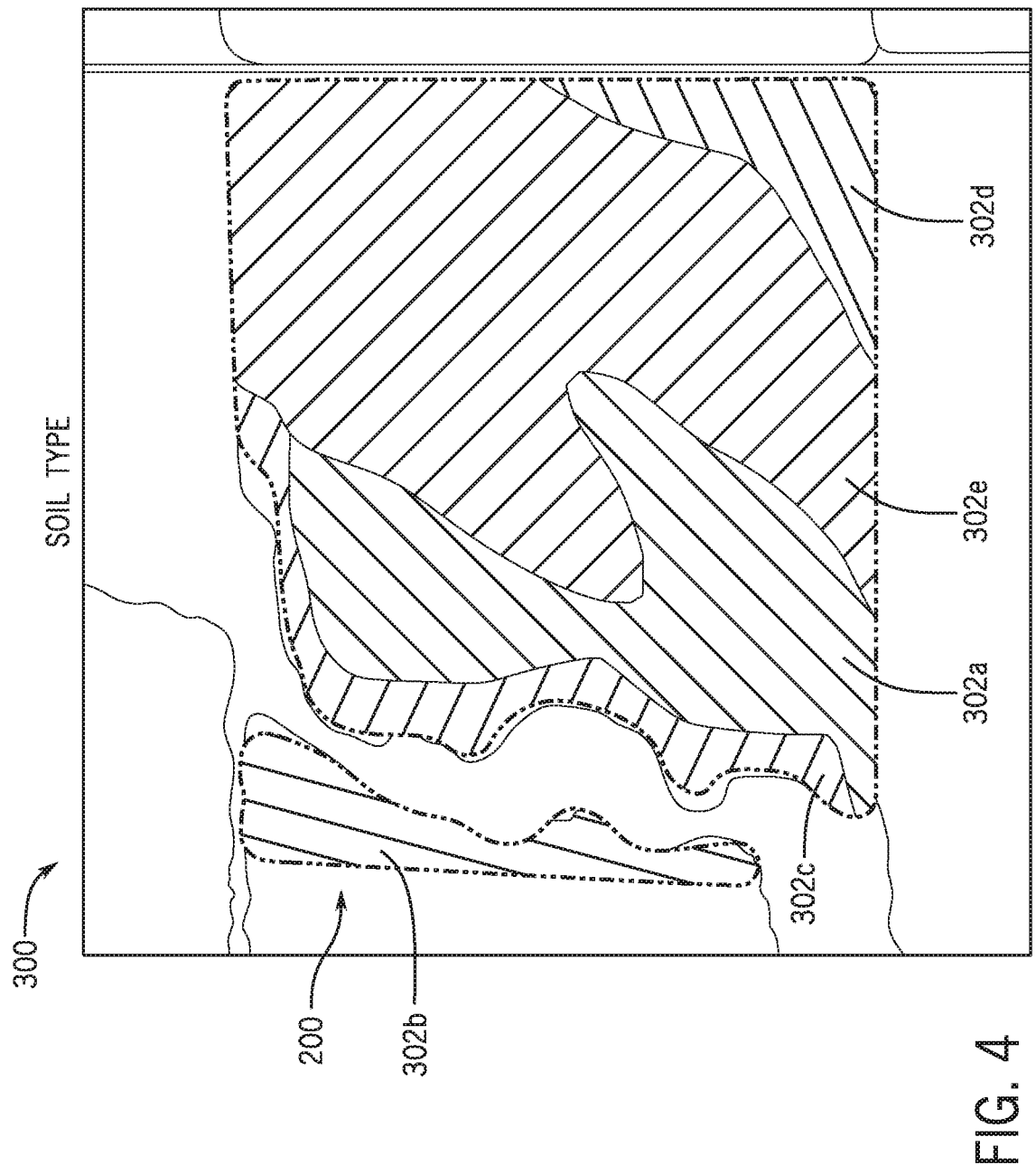
FIG. 4 is a soil type map for the field of FIG. 3 that may be used by the soil analysis system of FIG. 2 according to an example embodiment.

The view of FIG. 4 depicts a soil type map 300 for the field 200 on which similar soil types for sensor-based data sets are determined, clustered, and extrapolated as soil type zones 302a-302e overlaid one an image of the field 200. In one example, the analysis module 180 may, in effect, build such a map 300 for the field 200 by individually determining soil types of sampling locations (e.g., by sending location coordinates and receiving a soil type in response) over time such that the map 300 may be updated as additional soil data is collected and analyzed. In other examples, the soil type map 300 may be available from an external source, such as database 170.

In the example depicted in FIG. 4, the soil type zone 302a corresponds to clime silty clay on 1 to 3% slopes; soil type zone 302b corresponds to clime silty clay on 3 to 7% slopes; soil type zone 302c corresponds to Clime-Hobbs complex on 0 to 20% slopes; soil type zone 302d corresponds to Irwin silty clay loam at 1 to 3% slopes; and soil type zone 302e corresponds to Rosehill silty clay at 1 to 3% slopes. These soil types are merely examples. As shown, the soil type varies across the field 200. In any event, the soil type map 300 may be displayed to the operator via the display device 126 and/or stored for subsequent access in order to determine soil type in response to subsequent collection of sensor-based data sets. In some examples, the soil type map 300 may be provided in relative real time on the vehicle 110, including when the vehicle 110 is operating within the field.

As noted above, the analysis module 180 may also receive an infrared spectra representation in the near-infrared range and the mid-infrared range as part of the soil data set. Generally, the analysis module 180 processes the infrared spectra representations with infrared spectroscopy techniques in order to generate estimated nutrient values for the soil at the respective location.

Generally, infrared spectroscopy exploits the fact that molecules (e.g., molecules associated with nutrients or other soil characteristics) absorb frequencies that are characteristic of respective molecular structure. Such frequencies and associated wavelengths for particular nutrients and soil characteristics may be identified by comparing the spectra to reference spectra. In one example, one or more wavelength peaks may represent a nutrient or other soil characteristic. The value of such a nutrient or soil characteristic may be determined by application of a calibration (or standard) curve. The selection of the wavelength peaks and the subsequent application of the calibration curves may be dependent on a number of parameters, including soil type and other soil characteristics (e.g., moisture, pH, and temperature). Typically, a calibration curve operates as a mechanism for determining the concentration of a substance in an unknown sample by comparing the unknown to a set of standard samples of known concentration, e.g., based on empirical observations that may be extrapolated to samples of unknown concentrations. Each calibration curve may be linear or non-linear and generated with regression analysis or other modeling mechanisms, including neural network or machine learning techniques, discussed below.

Figure 5:
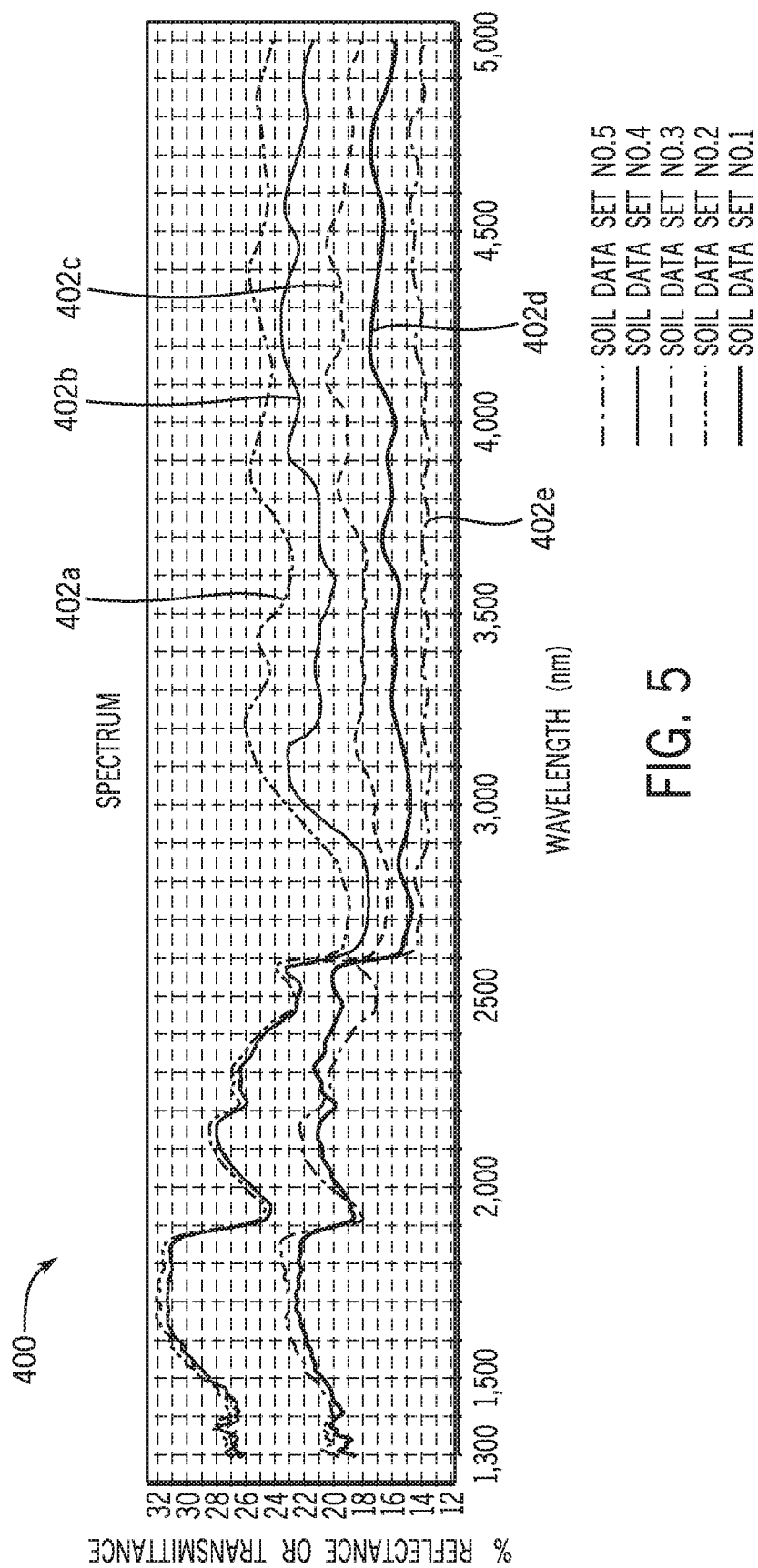
FIG. 5 is a sample spectra representation for the field of FIG. 3 collected by a sensor apparatus as part of the soil analysis system of FIG. 2 according to an example embodiment.

Briefly, reference is made to FIG. 5, which is an example infrared spectra plot 400 with spectra representations 402a-402e depicted for a sample collection of sensor-based soil data sets. In FIG. 5, the plot 400 includes wavelength represented on the horizontal axis and percentage (%) of reflection or transmittance represented on the vertical axis. As shown, spectra representations 402a-402e are depicted at wavelengths of 1300 nm-5000 nm, e.g., over at least portions of the near-infrared range and the mid-infrared range. During operation, the analysis module 180 operates to evaluate each of the infrared spectra representations 402a-402e, identify one or more of the wavelength peaks that correspond to the nutrients of interest, and apply one or more calibration curves to the one or more wavelength peaks in order to estimate or otherwise determine one or more nutrient values.

Returning to FIG. 2, in one example, the analysis module 180 may retrieve a calibration curve from the data storage 188 based on one or more of the location and/or soil type associated with the location. In particular, the data storage 188 may have one or more calibration curves that are calibrated according to the soil type such that the analysis module 180 may retrieve the calibration curve associated with the soil type for the location of the sensor-based soil data set. In some example, the calibration curve may be selected and/or modified based on parameters in addition to location and/or soil type, such as moisture, pH, temperature, and the like. In further examples, discussed below, the calibration curves of the data storage 188 may be derived or dependent on additional parameters, such as laboratory-based soil data sets. In effect, the calibration curves may be derived and/or otherwise enabled for the particular location and local characteristics of the soil data set, as opposed to a generalized calibration curve for a wider area or region. In particular, and as discussed in greater detail below, the selected calibration curves may initially be based on soil type and relatively generic known nutrient characteristics for that soil type; and in further examples, the calibration curves may be supplemented or modified based on laboratory testing of soil samples from the field of the operator and/or from fields of other operators with similar soil types. Such updated calibration curves may be generated with neural networks or machines learning techniques.

As such, the analysis module 180 generates one or more estimated nutrient values for the location associated with the soil data set. The estimated nutrient values may be provided to the display device 126 or other interface device for conveying the information to the operator.

Figure 6:
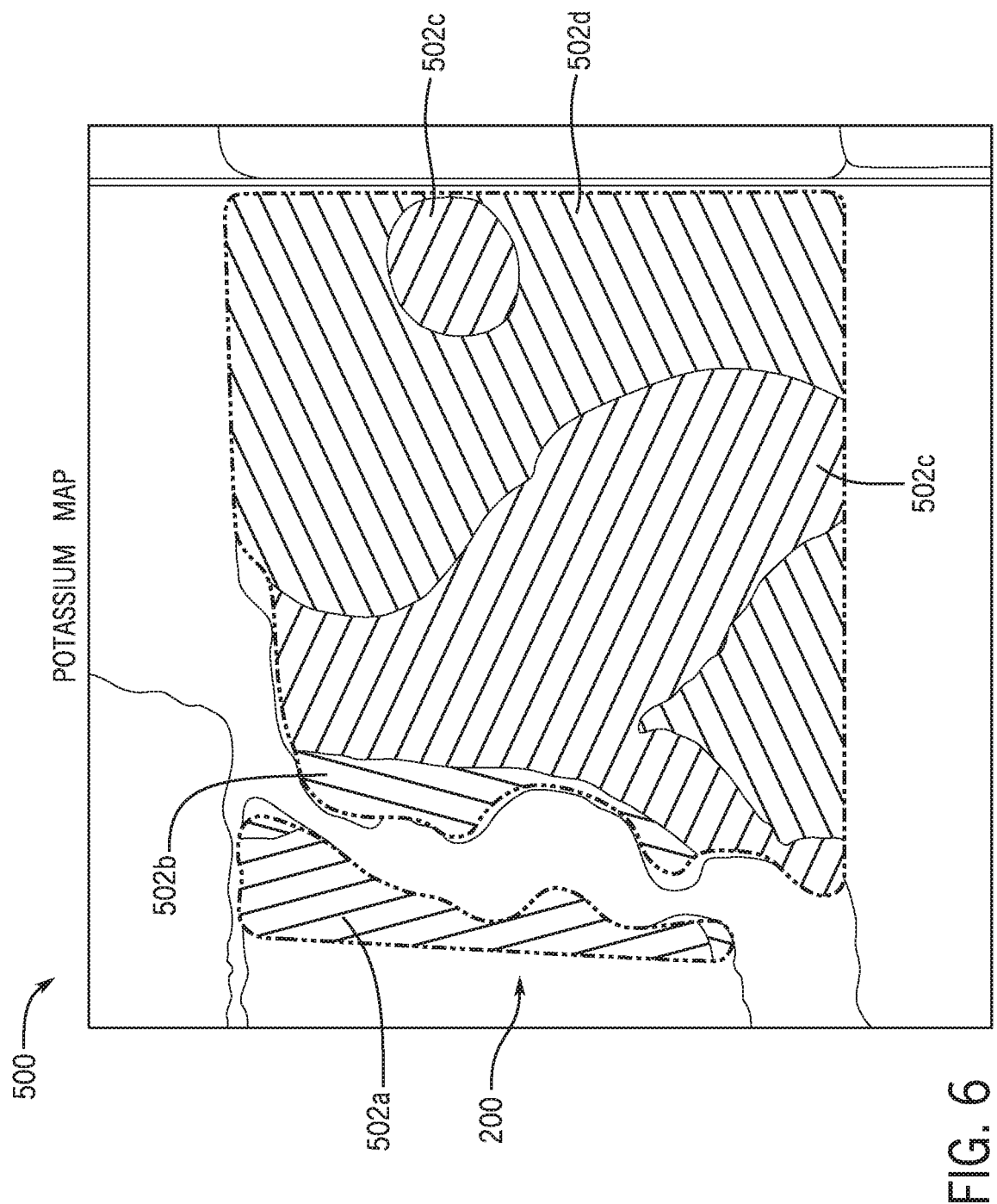
FIG. 6 is a sample nutrient zone map for the field of FIG. 3 generated by the soil analysis system of FIG. 2 according to an example embodiment.

Additionally, the estimated nutrient values and corresponding locations may be provided to the nutrient mapping module 182. Over time, the nutrient mapping module 182 operates to cluster similar nutrient values in adjacent locations to derive boundaries between areas with relative differences nutrient values as a nutrient zone map. Reference is made to FIG. 6, which is an example nutrient zone map 500 for the field 200 based on the sensor-based soil data sets discussed above. In this example, the nutrient mapping module 182 generates boundaries to define "zones" 502a-502d of generally similar nutrient values to form the nutrient zone map 500 for the field 200. The nutrient zone map 500 defined by the nutrient mapping module 182 may provide the operator with additional information about the field and enable each zone to be individually addressed with decisions. In this example, the nutrient zones 502a-502d respective represent different amounts of potassium as the nutrient, e.g. in which the soil of zone 502a has a relatively high amount of potassium as compared to the soil of zone 502b, and so on, to the zone 502d, which has soil with a relatively smaller amount of potassium. Although potassium is represented in map 500, other nutrient (or characteristic) zones may be provided, such as magnesium, phosphorus, moisture, pH, temperature, and the like. The nutrient zone map 500 may be provided to the display device 126, as well as data storage 188 to be distributed as necessary or desired to other modules 180, 182, 184, 186 of the controller 122. In some examples, the nutrient zone map 500 may be provided in relative real time on the vehicle 110, including when the vehicle 110 is operating within the field.

The recommendation module 184 receives nutrient zones from the nutrient mapping module 182. The recommendation module 184 evaluates the nutrient zones and, in response, may generate one or more types of recommendations. In particular, the recommendation module 184 may consider a nutrient value or values for a zone or zones; identify any deficiency or issue with respect to the nutrient value or values for the zone or zones; and generate a recommendation to remedy or otherwise address the deficiency or issue. As an example, the recommendation module 184 may consider the nutrient values for primary nutrients such as nitrogen, potassium, and phosphorus, and if such nutrients are deemed lacking in the respective zone, the recommendation module 184 may generate a fertilizer recommendation to supplement or otherwise improve the respective nutrient. The recommendation may be generated by the recommendation module 184 in any suitable manner, including with look-up tables, models, machine learning, equations, and the like based on historical, scientific, and/or empirical data.

Figure 7:
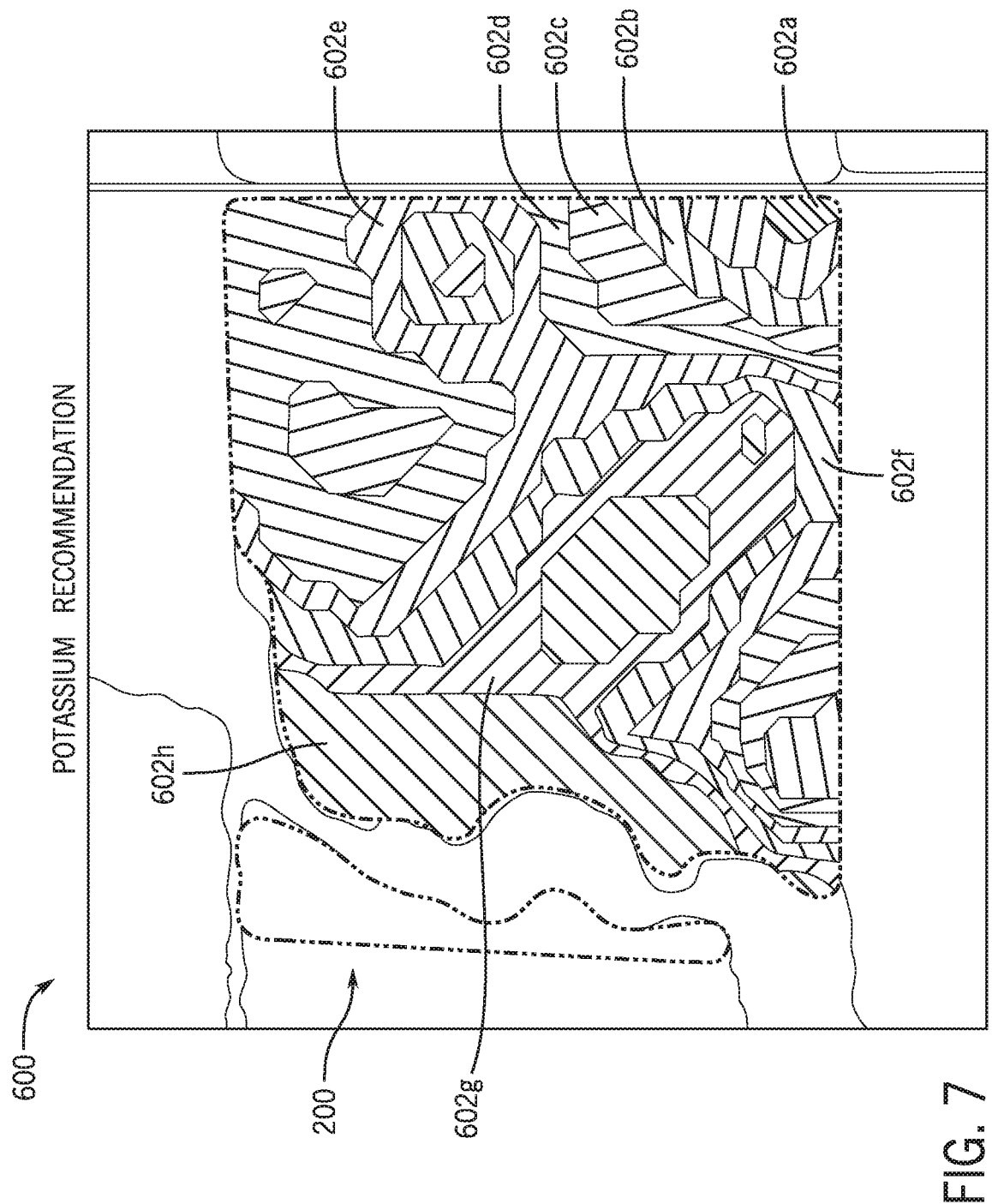
FIG. 7 is a recommendation map generated in response to the nutrient zone map of FIG. 6 by the soil analysis system of FIG. 2 according to an example embodiment.

Reference is made to FIG. 7, which is a nutrient recommendation map 600 of the field 200 in which a number of nutrient recommendation zones 602a-602h have been defined, for example, based on the nutrient zone map 500 of FIG. 6 with respect to potassium as the nutrient. As shown, the nutrient recommendation zones 602a-602h represent clustered areas, each of which have relatively similar additional amounts of nutrient that are recommended for the field. In this example, nutrient recommendation zone 602a requires a relative more additional amount of nutrient as compared to nutrient recommendation zone 602b, and so on, to nutrient recommendation zone 602h, which requires relatively little additional amount of nutrient. The recommendation module 184 may provide the nutrient recommendation map 600 to the display device 126 for consideration by the operator and/or stored in data storage 188.

Returning to FIG. 2, the nutrient recommendations, either individually or collectively, may be provided to the fertilizer applicator 134 in the form of actuator signals or commands. In particular, the controller 122 may command the fertilizer applicator 134 to dispense a specific amount of fertilizer at the respective location associated with the sensor-based soil data set in accordance with a value based on the generated nutrient recommendation. In other words, the soil analysis system 100 may dispense individual amounts of fertilizer based on the nutrient values and recommendations of the analyzed soil, either at the time and place of the sensor collection and soil analysis or subsequently. Such analysis and/or fertilizer application may occur prior to planting, during planting, or subsequent to planting. In some examples, the collection and analysis of sensor-based soil data sets, the generation of nutrient recommendations, and the appropriate application of fertilizer based on the nutrient recommendations may be automated or autonomous.

In one example, the recommendation module 184 may also consider the nutrient values within the nutrient zones within the context of the overall field or within an entire zone. In particular, the recommendation module 184 may identify areas or locations in which one or more soil data sets are absent, questionable, or potentially out of date. For example, the density of collected data sets for a zone or area may indicate the nature of variations in the nutrient values (e.g., greater variation requires more soil data sets for each area). In one example, the recommendation module 184 generates sampling recommendations with locations at which to take further samples or soil data sets. In addition to sampling recommendations and/or fertilizer recommendations, the recommendation module 184 may further generate seeding recommendations, soil amendment recommendations, watering recommendations, and/or other agricultural action recommendations. In some examples, the recommendation map 600 may be provided in relative real time on the vehicle 110, including when the vehicle 110 is operating within the field.

In one example, the sampling recommendations may include sensor collection recommendations in the form of locations at which additional soil data sets should be collected by the sensor apparatus 130. Such sampling recommendations may be provided to the operator via an interface, such as the display device 126 or to a system (e.g., an automated navigation or planning system) that may implement collection of additional soil data sets. In other examples, the sampling recommendations may include soil collection recommendations in the form of locations at which physical soil samples should be collected by the sampling mechanism 132 for laboratory analysis, as discussed in greater detail below. Such sampling recommendations may be provided to the operator via an interface, such as the display device 126.

Additionally, and as functionally depicted in FIG. 2, the sampling recommendations in the form of soil collection recommendations may be provided to a sampling mechanism 132 to implement collection of soil samples. Generally, the soil samples resulting from the soil collection recommendations may be analyzed according to laboratory testing to generate actual nutrient values. As such, and as described in greater detail below, a soil collection recommendation may be used to generate actual nutrient values for a location, which in turn, may be used to evaluate the estimated nutrient values and the associated location-based calibration curve for the respective location corresponding to the actual nutrient values.

In one example, the feedback module 186 receives at least a portion of the sensor-based soil data sets, the estimated nutrient values, at least a portion of the laboratory-based soil data sets, and the actual nutrient values. The feedback module 186 may also receive and/or consider the location-based calibration curves used to generate the estimated nutrient values. Generally, the feedback module 186 operates to evaluate the estimated nutrient values and the underlying location-based calibration curves in view of the actual nutrient values for a corresponding location. Ideally, the estimated nutrient values will be identical to the actual nutrient values. However, if the estimated nutrient values differ from the actual nutrient values, the feedback module 186 may modify or update the location-based calibration curves as location-based calibration curve updates, which may replace or modify one or more of the location-based calibration curves stored in data storage 188.

Figure 8:
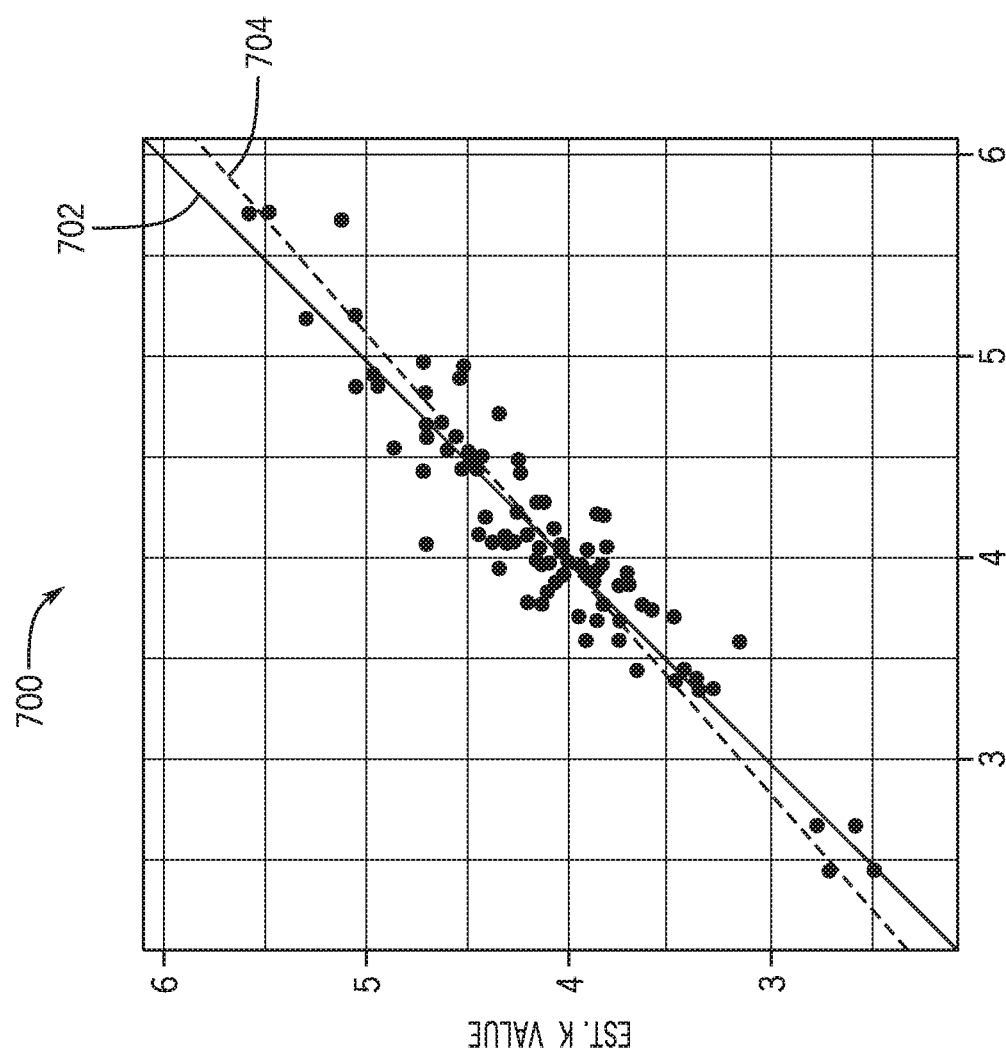
FIG. 8 is a sample validation report generated in response to the nutrient zone map of FIG. 6 by the soil analysis system of FIG. 2 according to an example embodiment.

As an example, reference is briefly made to FIG. 8, which is an example plot 700 for potassium values with actual nutrient values for potassium represented on the horizontal axis and estimated nutrient values for potassium represented on the vertical axis. Ideally, the values would match one another, as represented by ideal line 702. However, in this example, the values are skewed slightly such that a validation line 704 fit to the data of the plot 700 is offset relative to the ideal line 702. Based on this type of feedback, the feedback module 186 may modify the calibration curves that generated the estimated nutrient values such that subsequent soil analysis results in estimated nutrient values better approximating the actual nutrient values, e.g. such that the validation line 704 is closer to the ideal line 702.

The feedback module 186 may operate to update the location-based calibration curves in any suitable manner. In one example, the feedback module 186 may be supplemented or modified based on laboratory testing of soil samples from the field of the operator, as discussed above, and/or from other operators with similar soil types. Such updated calibration curves may be generated by neural network algorithms with machines learning techniques.

As appearing herein and generally referring to the feedback module 186, the term "neural network" algorithm refers to a computer-readable program having a structure composed of multiple layers of interconnected nodes or neurons. The particular structure of a neural network algorithm (when employed) will vary between embodiments of the present disclosure, noting that several types of neural network algorithms currently exist and additional neural network types continue to be developed. Generally, a neural network algorithm may include an input layer into which data is fed (e.g., the estimated nutrient values generated from sensor-based soil data sets and actual nutrient values generated from laboratory-based soil data sets); a final output layer at which processing results appear; and any number of hidden layers between the input and output layers. Each node contained in a given layer of the neural network algorithm may be connected to some, if not all of the nodes in a subsequent network layer, thereby forming a processing structure loosely akin to a biological neural network. Additionally, the behavior or performance of a neural network algorithm may be modified by adjusting certain parameters associated with the nodes and connections of the neural network, including the activation strength or "weight" between node-to-node connections and, in many cases, an inactivity bias assigned to each node. Through iteratively modifying such parameters using feedback data, the neural network algorithm may be trained to improve the algorithm performance; that is, the tendency of the algorithm to provide a correct or desired result across a range input data sets. Such training may be considered "machine learning" when largely automated by providing the neural network algorithm with feedback data (which may be expressed using cost functions, as an example), with the neural network algorithm or an associated algorithm iteratively adjusting the network parameters (e.g., node-to-node weights and inactivity biases) without reliance or with a reduced reliance on direct human programming, to gradually improve the performance of the neural network algorithm.

By the nature of the neural network algorithm of the feedback module 186, the accuracy of the estimated nutrient values should improve over time as additional soil samples are collected and as additional relationships between the various soil parameters discussed herein are recognized. The accuracy improvements should occur with respect to an individual field of the operator; and additionally, may occur with respect to other fields and other operators as the derived and recognized parameter relationships and more nuanced calibration curves are applied across a collective or wider soil analysis system 100.

In any event, the updates to the calibration curves are provided to data storage 188 such that the analysis module 180 may access the updated location-based calibration curves for evaluation of subsequent sensor-based soil data sets, thereby improving the accuracy of the estimated nutrient values.

In some examples, the functions of the feedback module 186 may be performed by the soil analysis center 150 (FIG. 1). In this manner, some determinations or conclusions gleaned from one operator or field may be considered with respect to other operators or fields. Similarly, the functions of one or more of the other modules 180, 182, 184 may be performed by the soil analysis center 150.

Accordingly, the soil analysis system 100 provides relatively immediate and clear representations of soil characteristics for the operator. The soil analysis system 100 provides such representations for the particular field of the operator, including soil type maps, soil nutrient maps, nutrient recommendation maps, and sampling recommendations. Moreover, continued use of the soil analysis system 100 provides feedback that operates to improve the soil analysis. As a result, the soil analysis system 100 may provide an increased crop yield and more efficient use of time, water, and/or fertilizer, as well as decreases in human labor and financial costs for soil testing.

Although not shown, operation of the soil analysis system 100 discussed above may also be expressed as a method performing the operational steps in accordance with the present disclosure. Such methods may be implemented with respect to one or more vehicles in combination with a soil analysis center, a single vehicle, and/or the soil analysis center cooperating with one or more vehicles. As can be appreciated in light of the disclosure, the order of operation is not limited to a sequential execution described above, but may be performed in one or more varying orders as applicable and in accordance with the present disclosure. Further one or more operational steps may be omitted and/or additional steps added.

Also, the following examples are provided, which are numbered for easier reference.

1. A soil analysis system for an agricultural vehicle, comprising: a sensor apparatus including: a location sensor configured to determine a location of the agricultural vehicle; and an infrared sensor configured to collect infrared spectra from soil at the location; a controller coupled to the location sensor and the infrared sensor and configured to: determine a soil type based on the location; select at least one nutrient calibration curve based on the soil type at the location; analyze the infrared spectra according to the at least one nutrient calibration curve to generate at least one estimated nutrient value for the soil at the location; and generate display commands representing the at least one estimated nutrient value; and a display device coupled to the controller and configured to generate a first display representing the at least one estimated nutrient value based on the display commands.
2. The soil analysis system of example 1, further comprising a vehicle communication component coupled to the controller, wherein the controller is further configured to determine the soil type by accessing a soil type mapping database via the vehicle communication component.
3. The soil analysis system of example 1, wherein the sensor apparatus, the controller, and the display device are positioned on the agricultural vehicle.
4. The soil analysis system of example 1, wherein the infrared sensor includes a near-infrared sensor.
5. The soil analysis system of example 1, wherein the infrared sensor includes a mid-infrared sensor.
6. The soil analysis system of example 1, wherein the sensor apparatus further includes a light source.
7. The soil analysis system of example 1, wherein the infrared sensor is a near-infrared sensor, wherein the sensor apparatus further includes a mid-infrared sensor and a light source, and wherein the near-infrared sensor, the mid-infrared sensor, and the light source are positioned on the agricultural vehicle.
8. The soil analysis system of example 1, wherein the controller is configured to: determine a series of the at least one estimated nutrient values over a corresponding series of locations and infrared spectra; and generate a nutrient zone map in which boundaries of nutrient zones are formed based on the series of the at least one estimated nutrient values for display on the display device.
9. The soil analysis system of example 8, wherein the controller is further configured to evaluate each of the nutrient zones and generate a nutrient recommendation map with recommendation zones indicating an amount of nutrient recommended for each of the nutrient zones for display on the display device.
10. The soil analysis system of example 9, wherein the controller is further configured to generate soil sampling recommendations based on the nutrient zones for display on the display device.
11. The soil analysis system of example 1, wherein the controller is further configured to: receive at least one actual nutrient value for the location based on at least one soil sample; and update the at least one nutrient calibration curve based on the at least one actual nutrient value.
12. The soil analysis system of example 11, wherein the controller is configured to update the at least one nutrient calibration curve with a neural network based on machine learning.
13. The soil analysis system of example 1, further comprising a vehicle communication component coupled to the controller, and wherein the controller is further configured to receive updates for the at least one nutrient calibration curve based on at least one actual nutrient value from a soil analysis center received by the controller via the vehicle communication component.
14. A soil analysis system arranged on-board an agricultural vehicle and comprising a controller having a processor and memory coupled to the processor and storing instructions, the processor executing the stored instructions to: receive a first sensor-based data set with first infrared spectra collected by a sensor apparatus at a first location within a field; determine a first soil type associated with the first location; select a first calibration curve corresponding to the first soil type at the first location; apply the first calibration curve to the first infrared spectra to generate a first estimated nutrient value for the first location; generate a fertilizer recommendation based on the first estimated nutrient value for the first location; and generate actuator signals to selectively apply a fertilizer onto the field at the first location based on the fertilizer recommendation.
15. The soil analysis system of example 14, wherein the processor further executes the stored instructions to: receive additional sensor-based data sets with additional infrared spectra collected by the sensor apparatus at additional locations within the field; determine respective soil types associated with the additional locations; select respective calibration curves corresponding to the respective soil types at the additional locations; apply the respective calibration curves to the additional infrared spectra to generate respective estimated nutrient values for the additional locations; and generate additional actuator signals to selectively apply the fertilizer onto the field at the additional locations based on the respective estimated nutrient values for the additional locations.

As will be appreciated by one skilled in the art, certain aspects of the disclosed subject matter can be embodied as a method, system (e.g., a work machine control system included in a work machine), or computer program product. Accordingly, certain embodiments can be implemented entirely as hardware, entirely as software (including firmware, resident software, micro-code, etc.) or as a combination of software and hardware (and other) aspects. Furthermore, certain embodiments can take the form of a computer program product on a computer-usable storage medium having computer-usable program code embodied in the medium.

As will be appreciated by one skilled in the art, aspects of the disclosed subject matter can be described in terms of methods, systems (e.g., control or display systems deployed onboard or otherwise utilized in conjunction with work machines), and computer program products. With respect to computer program products, in particular, embodiments of the disclosure may consist of or include tangible, non-transitory storage media storing computer-readable instructions or code for performing one or more of the functions described throughout this document. As will be readily apparent, such computer-readable storage media can be realized utilizing any currently-known or later-developed memory type, including various types of random access memory (RAM) and read-only memory (ROM). Further, embodiments of the present disclosure are open or "agnostic" to the particular memory technology employed, noting that magnetic storage solutions (hard disk drive), solid state storage solutions (flash memory), optimal storage solutions, and other storage solutions can all potentially contain computer-readable instructions for carrying-out the functions described herein. Similarly, the systems or devices described herein may also contain memory storing computer-readable instructions (e.g., as any combination of firmware or other software executing on an operating system) that, when executed by a processor or processing system, instruct the system or device to perform one or more functions described herein. When locally executed, such computer-readable instructions or code may be copied or distributed to the memory of a given computing system or device in various different manners, such as by transmission over a communications network including the Internet. Generally, then, embodiments of the present disclosure should not be limited to any particular set of hardware or memory structure, or to the particular manner in which computer-readable instructions are stored, unless otherwise expressly specified herein.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be non-transitory and can be any computer readable medium that is not a computer readable storage medium and that can communicate, propagate, or transport a program for use by or in connection with an instruction execution system, apparatus, or device.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality. The term module may be synonymous with unit, component, subsystem, sub-controller, circuitry, routine, element, structure, control section, and the like.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of work vehicles.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Aspects of certain embodiments are described herein can be described with reference to flowchart illustrations and/or block diagrams of methods, apparatus (systems) and computer program products according to embodiments of the invention. It will be understood that each block of any such flowchart illustrations and/or block diagrams, and combinations of blocks in such flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions can also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Any flowchart and block diagrams in the figures, or similar discussion above, can illustrate the architecture, functionality, and operation of possible implementations of systems, methods and computer program products according to various embodiments of the present disclosure. In this regard, each block in the flowchart or block diagrams can represent a module, segment, or portion of code, which comprises one or more executable instructions for implementing the specified logical function(s). It should also be noted that, in some alternative implementations, the functions noted in the block (or otherwise described herein) can occur out of the order noted in the figures. For example, two blocks shown in succession (or two operations described in succession) can, in fact, be executed substantially concurrently, or the blocks (or operations) can sometimes be executed in the reverse order, depending upon the functionality involved. It will also be noted that each block of any block diagram and/or flowchart illustration, and combinations of blocks in any block diagrams and/or flowchart illustrations, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A soil analysis system for an agricultural vehicle, comprising:
    a sensor apparatus including:
        a location sensor configured to determine a location of the agricultural vehicle; and
        an infrared sensor configured to collect infrared spectra from soil while the soil remains situated in the ground of a field at the location;
    a controller coupled to the location sensor and the infrared sensor and configured to:
        access a soil type mapping database to determine a soil type based on the location;
        select a nutrient calibration curve based on the soil type at the location according to the soil type mapping database, the nutrient calibration curve encompassing multiple wavelengths;
        analyze the infrared spectra to identify a wavelength peak corresponding to a nutrient of interest in the soil and apply the nutrient calibration curve to the wavelength peak to determine an estimated nutrient value for the soil at the location; and
        generate display commands representing the estimated nutrient value; and
    a display device coupled to the controller and configured to generate a first display representing the estimated nutrient value based on the display commands.

2. The soil analysis system of claim 1, further comprising a vehicle communication component coupled to the controller, wherein the controller accesses the soil type mapping database via the vehicle communication component.

3. The soil analysis system of claim 1, wherein the sensor apparatus, the controller, and the display device are positioned on the agricultural vehicle.

4. The soil analysis system of claim 1, wherein the infrared sensor includes a near-infrared sensor.

5. The soil analysis system of claim 1, wherein the infrared sensor includes a mid-infrared sensor.

6. The soil analysis system of claim 1, wherein the sensor apparatus further includes a light source.

7. The soil analysis system of claim 1, wherein the infrared sensor is a near-infrared sensor, wherein the sensor apparatus further includes a mid-infrared sensor and a light source, and wherein the near-infrared sensor, the mid-infrared sensor, and the light source are positioned on the agricultural vehicle.

8. The soil analysis system of claim 1, wherein the controller is configured to:
    determine a series of the estimated nutrient values over a corresponding series of locations and infrared spectra; and
    generate a nutrient zone map in which boundaries of nutrient zones are formed based on the series of the estimated nutrient values for display on the display device.

9. The soil analysis system of claim 8, wherein the controller is further configured to evaluate each of the nutrient zones and generate a nutrient recommendation map with recommendation zones indicating an amount of nutrient recommended for each of the nutrient zones for display on the display device.

10. The soil analysis system of claim 9, wherein the controller is further configured to generate soil sampling recommendations based on the nutrient zones for display on the display device.

11. The soil analysis system of claim 1, wherein the controller is further configured to:
    receive an actual nutrient value for the location based on a soil sample; and
    update the nutrient calibration curve based on the actual nutrient value.

12. The soil analysis system of claim 11, wherein the controller is configured to update the nutrient calibration curve with a neural network based on machine learning.

13. The soil analysis system of claim 1, further comprising a vehicle communication component coupled to the controller, and wherein the controller is further configured to receive updates for the nutrient calibration curve based on an actual nutrient value from a soil analysis center received by the controller via the vehicle communication component.

14. A soil analysis system arranged on-board an agricultural vehicle and comprising a controller having a processor and memory coupled to the processor and storing instructions, the processor executing the stored instructions to:
    receive a first sensor-based data set with first infrared spectra collected by a sensor apparatus of soil while the soil remains situated in the ground at a first location within a field;
    analyze the first infrared spectra to identify a first wavelength peak corresponding to a first nutrient of interest in the soil;
    access a soil type mapping database to determine a first soil type associated with the first location;
    select a first calibration curve corresponding to the first soil type at the first location according to the soil type mapping database, the first calibration curve encompassing multiple wavelengths;
    apply the first calibration curve to the first wavelength peak of the first infrared spectra to determine a first estimated nutrient value for the first location;
    generate a fertilizer recommendation based on the first estimated nutrient value for the first location; and
    generate actuator signals to selectively apply a fertilizer onto the field at the first location based on the fertilizer recommendation.

15. The soil analysis system of claim 14, wherein the processor further executes the stored instructions to:
receive additional sensor-based data sets with additional infrared spectra collected by the sensor apparatus of soil while the soil remains situated in the ground at additional locations within the field;
access the soil type mapping database to determine respective soil types associated with the additional locations;
select respective calibration curves corresponding to the respective soil types at the additional locations according to the soil type mapping database;
apply the respective calibration curves to the additional infrared spectra to generate respective estimated nutrient values for the additional locations; and
generate additional actuator signals to selectively apply the fertilizer onto the field at the additional locations based on the respective estimated nutrient values for the additional locations.

16. The soil analysis system of claim 15, wherein the processor further executes the stored instructions to generate a nutrient zone map from the first estimated nutrient value and the respective estimated nutrient values with nutrient zones.

17. The soil analysis system of claim 16, wherein the processor further executes the stored instructions to generate a nutrient recommendation map from the nutrient zone map with a nutrient recommendation for each of the nutrient zones.

18. The soil analysis system of claim 17, wherein the processor further executes the stored instructions to generate soil sampling recommendations based on the nutrient zones.

19. The soil analysis system of claim 14, wherein the processor further executes the stored instructions to update the first calibration curve based on an actual nutrient value for the first location.

20. A method for analyzing soil on-board an agricultural vehicle within a field, the method comprising the steps of:
collecting, with an infrared sensor, infrared spectra from the soil while the soil remains situated in the ground at a first location;
identifying, with a location sensor, the first location;
analyzing the infrared spectra to identify a wavelength peak corresponding to a nutrient of interest in the soil;
accessing a soil type mapping database to determine a soil type for the soil based on the first location;
selecting a nutrient calibration curve based on the soil type at the first location according to the soil type mapping database, the nutrient calibration curve encompassing multiple wavelengths;
applying the nutrient calibration curve to the wavelength peak of the infrared spectra in order to generate an estimated nutrient value for the soil at the first location; and
displaying, on a display device, the estimated nutrient value.

* * * * *